United States Patent
Xing et al.

(10) Patent No.: US 10,962,545 B2
(45) Date of Patent: Mar. 30, 2021

(54) METHODS AND COMPOSITIONS FOR THE DIAGNOSIS AND TREATMENT OF CANCER

(71) Applicants: BGI TECH SOLUTIONS CO., LTD, Guangdong (CN); BEIJING INSTITUTE FOR CANCER RESEARCH, Beijing (CN)

(72) Inventors: Rui Xing, Beijing (CN); Youyong Lu, Beijing (CN); Zhibo Gao, Beijing (CN); Wenmei Li, Beijing (CN); Jiantao Cui, Beijing (CN); Lin Li, Beijing (CN); Longyun Chen, Beijing (CN)

(73) Assignees: BGI TECH SOLUTIONS CO., LTD, Guangdong (CN); BEIJING INSTITUTE FOR CANCER RESEARCH, Beijing (CN)

( * ) Notice: Subject to any disclaimer, the term of this patent is extended or adjusted under 35 U.S.C. 154(b) by 221 days.

(21) Appl. No.: 16/102,587

(22) Filed: Aug. 13, 2018

(65) Prior Publication Data

US 2019/0072561 A1 Mar. 7, 2019

Related U.S. Application Data

(62) Division of application No. 14/869,724, filed on Sep. 29, 2015, now Pat. No. 10,073,100.

(51) Int. Cl.
  *C12Q 1/6886* (2018.01)
  *G01N 33/574* (2006.01)
  *C07K 16/28* (2006.01)

(52) U.S. Cl.
  CPC ..... *G01N 33/57492* (2013.01); *C12Q 1/6886* (2013.01); *G01N 33/57446* (2013.01); *C07K 16/2833* (2013.01); *C12Q 2600/118* (2013.01); *C12Q 2600/156* (2013.01); *G01N 2333/5434* (2013.01); *G01N 2333/70539* (2013.01); *G01N 2333/70596* (2013.01)

(58) Field of Classification Search
  CPC .................................................. C12Q 1/6886
  USPC ...................................................... 435/7.23
  See application file for complete search history.

(56) References Cited

U.S. PATENT DOCUMENTS 10,073,100 B2  9/2018  Xing et al.

OTHER PUBLICATIONS

Nagarajan et al (Genome Biology, 2012, 13(R115): 1-10).*
Weiss et al (PLoS One, 2012, 7(5)(e37029): 1-8).*
Delahayel et al., "Alternatively, spliced NKp30 isoforms affect the prognosis of gastrointestinal stromal tumors," Nature Medicine, 9 pages, doi: 10.1038/nm.2366, (2011).
Dutta et al., "Analysis of Human Lymphocyte Antigen Class I Expression in Gastric Cancer by Reverse Transcriptase—Polymerase Chain Reaction," Human Immunology, 66:164-169, (2005).
Ishigami et al., "HLA-G Expression in Gastric Cancer," Anticancer Research, 26:2467-2472, (2006).
Ishigami et al., "Title," Cancer, 88(3):577-583, (2000). [Abstract Only].
Koch et al., "Activating natural cytotoxicity receptors of natural killer cells in cancer and infection," Trends in Immunology, 34(4). 182-191, doi: http://dx.doi.org/10.1016/j.it.2013.01.003, (2013).
Shen et al., "Relationship between the downregulation of HLA class I antigen and clinicopathological significance in gastric cancer," World J Gastroenterol, 11(23): 3628-3631, (2005).
Tockman et al., "Considerations in Bringing a Cancer Biomarker to Clinical Application," Cancer Res., 52:2711s-2718s, (1992).
Ueda et al., "Clinical Significance of HLA Class I Heavy Chain Expression in Patients With Gastric Cancer," Journal of Surgical Oncology, 95:451-455, (2008).
Ye et al., "Hypermethylation of HLA class I gene is associated with HLA class I down-regulation in human gastric cancer," Tissue Antigens, 75(1):30-39, (2010).
Yie et al., "Expression of Human Leukocyte Antigen G (HLA-G) Correlates with Poor Prognosis in Gastric Carcinoma," Annals of Surgical Oncology, 14(10):2721-2729, doi: 10.1245/s10434-007-9464-y, (2007).
U.S. Appl. No. 14/869,724, Final Office Action dated Feb. 27, 2018.
U.S. Appl. No. 14/869,724, Non-Final Office Action dated Sep. 27, 2017.
U.S. Appl. No. 14/869,724, Notice of Allowance dated May 11, 2018.
U.S. Appl. No. 14/869,724, Requirement for Restriction/Election dated Jun. 16, 2017.
U.S. Appl. No. 14/869,724, filed Sep. 29, 2015, U.S. Pat. No. 10,073,100, Patented.

* cited by examiner

*Primary Examiner* — Sean E Aeder

(74) *Attorney, Agent, or Firm* — Alston & Bird LLP

(57) ABSTRACT

The present invention relates to methods, kits, and compositions for detecting and/or diagnosing metastatic potential of cancer cells or for evaluating prognosis in a patient with cancer by detection of the protein expression level of an HLA class I molecule and/or the copy number variation of a polynucleotide encoding the HLA class I molecule. The present invention also relates to the use of the protein expression level of an HLA class I molecule and/or the copy number variation of a polynucleotide encoding the HLA class I molecule as a prognosis biomarker and metastasis predictive biomarker of cancer.

2 Claims, 9 Drawing Sheets

Specification includes a Sequence Listing.

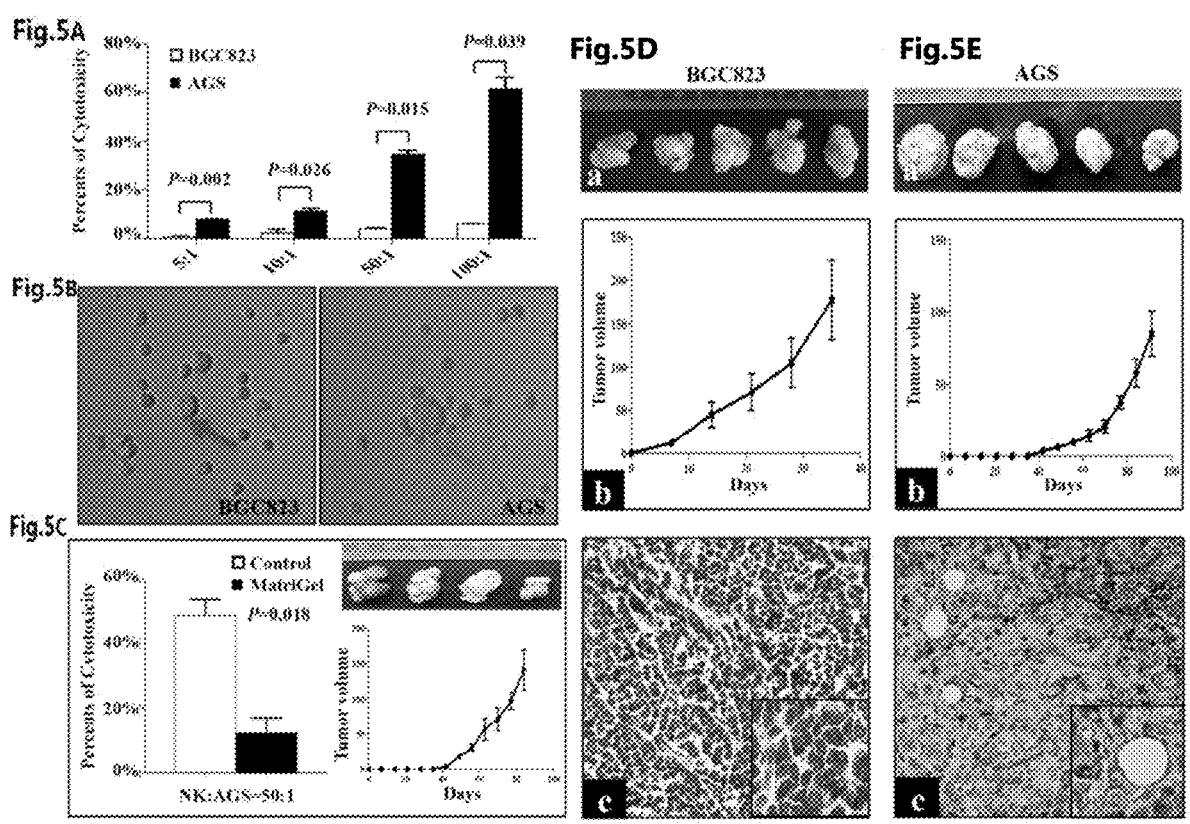

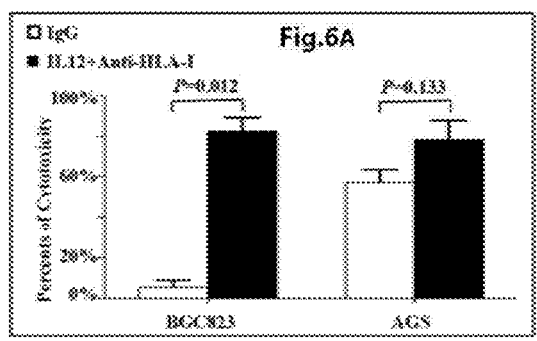
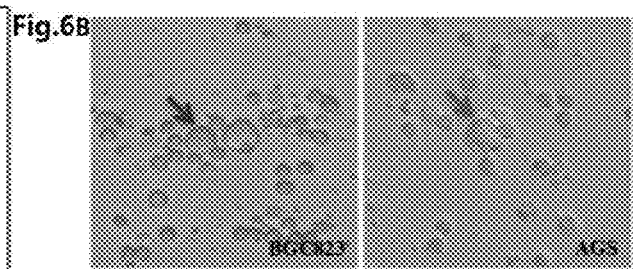
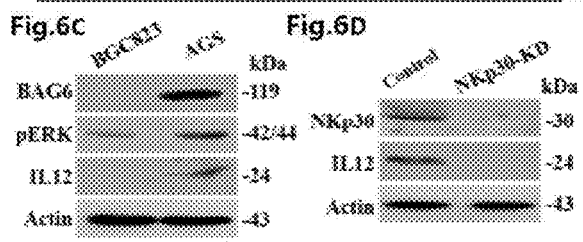
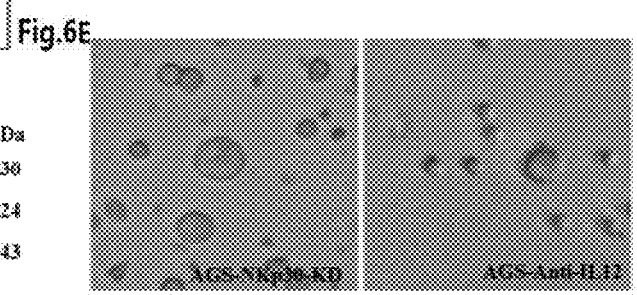

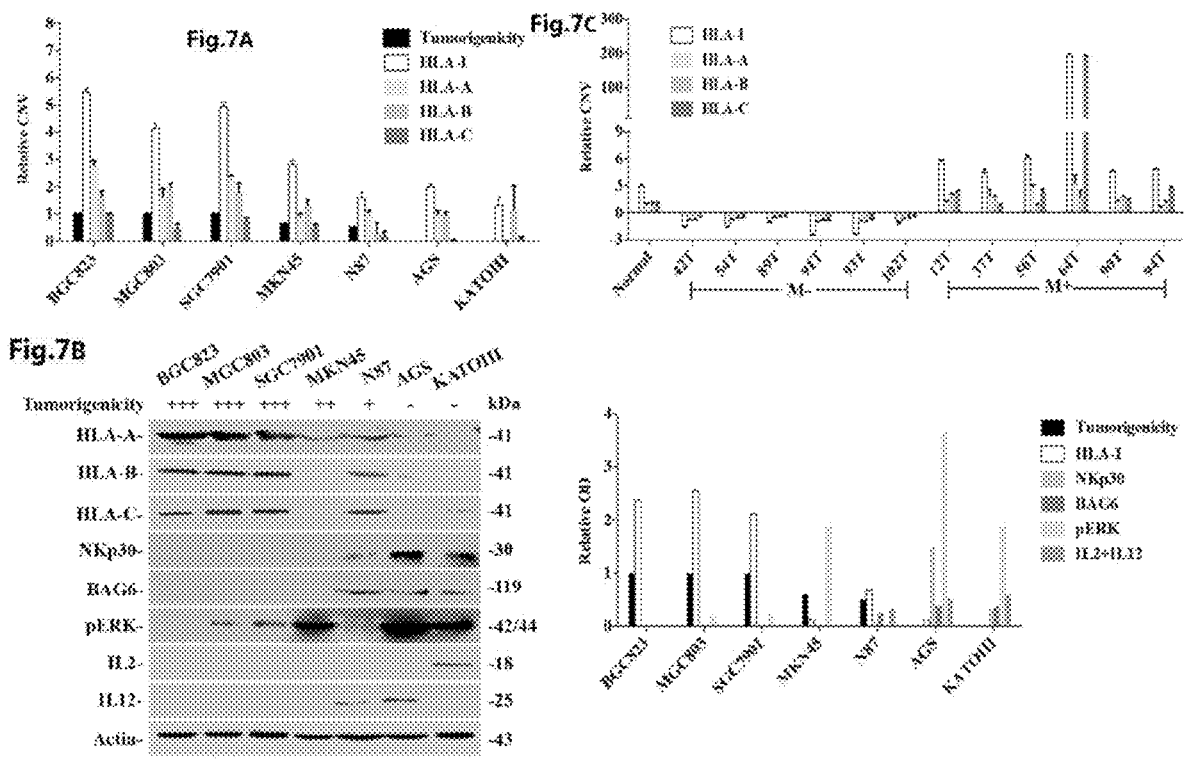

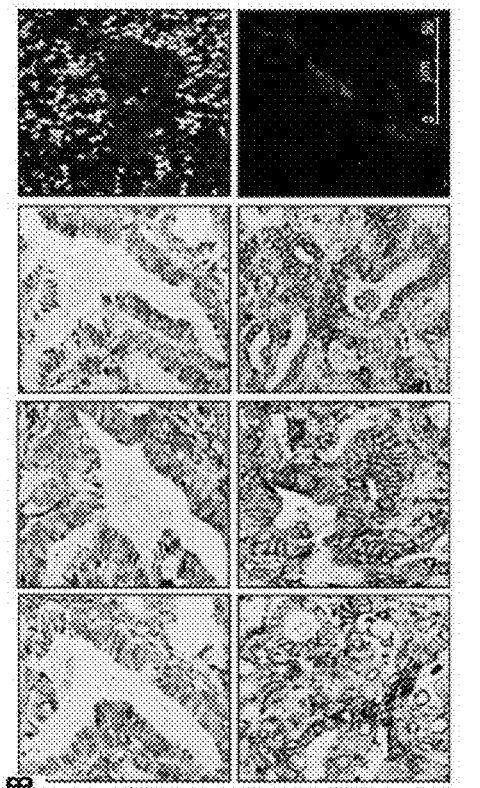
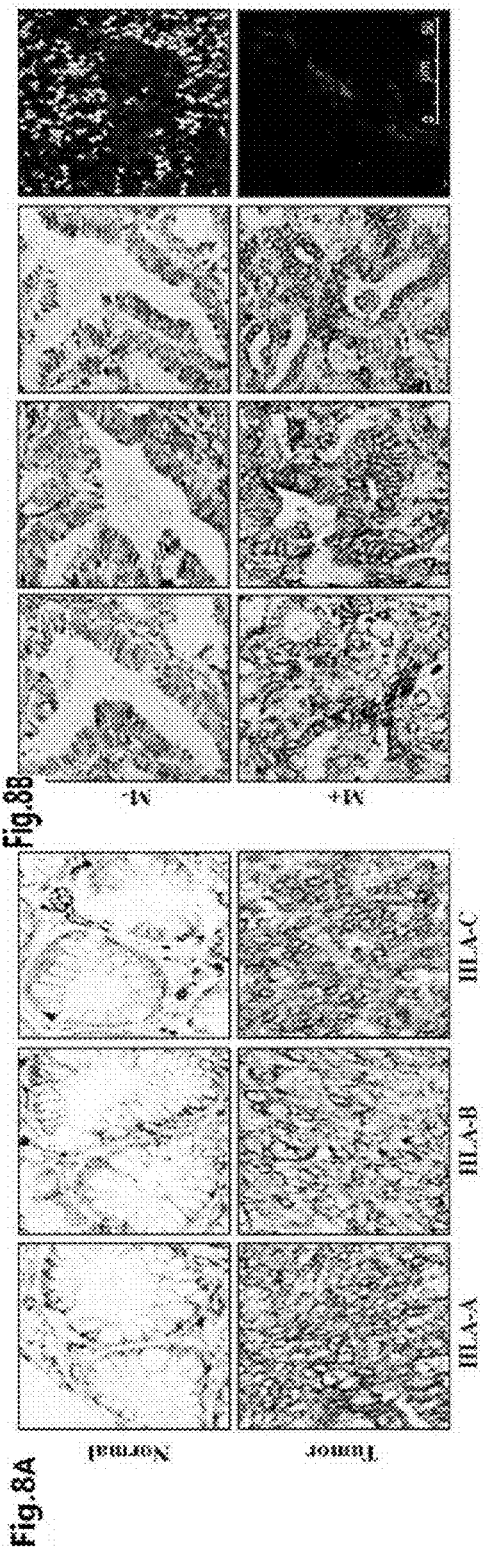
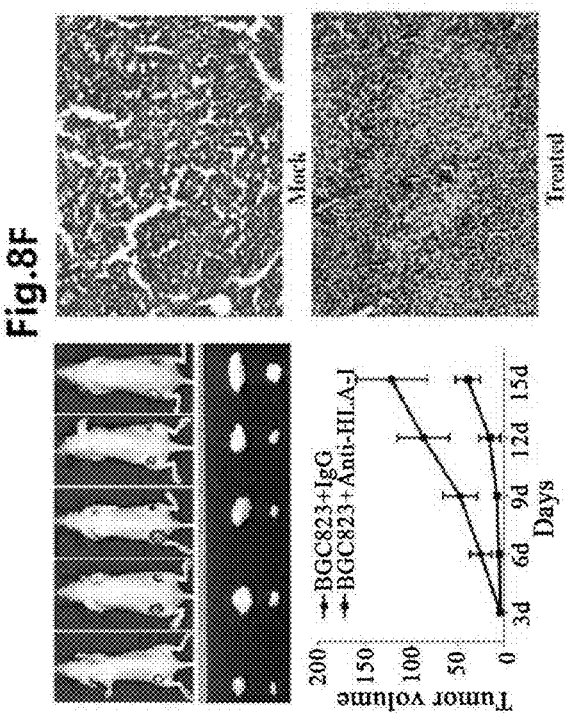
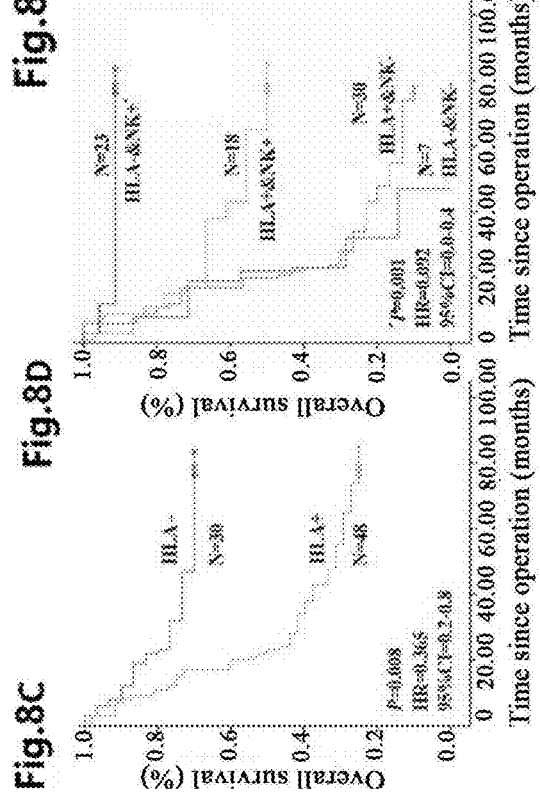

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: LINE-1

<400> SEQUENCE: 1
aaagccgctc aactacatgg                    20

<210> SEQ ID NO 2
<211> LENGTH: 21
<212> TYPE: DNA
<213> ORGANISM: Artificial sequence
<220> FEATURE:
<223> OTHER INFORMATION: LINE-1

<400> SEQUENCE: 2
tgctttgaat gcgtcccaga g                  21

<210> SEQ ID NO 3
<211> LENGTH: 20
<212> TYPE: DNA
<213> ORGANISM: Artificial Sequence
<220> FEATURE:
<223> OTHER INFORMATION: HLA-A

<400> SEQUENCE: 3
gtaaggaggg agatgggggt                    20

```
<210> SEQ ID NO 4
<211> LENGTH: 20
<212> TYPE: DNA
<213> ORGANISM: Artificial sequence
<220> FEATURE:
<223> OTHER INFORMATION: HLA-A

<400> SEQUENCE: 4
cagcaatgat gcccacgatg                                           20

<210> SEQ ID NO 5
<211> LENGTH: 20
<212> TYPE: DNA
<213> ORGANISM: Artificial sequence
<220> FEATURE:
<223> OTHER INFORMATION: HLA-B

<400> SEQUENCE: 5
tgagatgggg taaggagggg                                           20

<210> SEQ ID NO 6
<211> LENGTH: 20
<212> TYPE: DNA
<213> ORGANISM: Artificial sequence
<220> FEATURE:
<223> OTHER INFORMATION: HLA-B

<400> SEQUENCE: 6
cacaactgct aggacagcca                                           20

<210> SEQ ID NO 7
<211> LENGTH: 20
<212> TYPE: DNA
<213> ORGANISM: Artificial sequence
<220> FEATURE:
<223> OTHER INFORMATION: HLA-C

<400> SEQUENCE: 7
gtccagaacc cacaactgct                                           20

<210> SEQ ID NO 8
<211> LENGTH: 20
<212> TYPE: DNA
<213> ORGANISM: Artificial sequence
<220> FEATURE:
<223> OTHER INFORMATION: HLA-C

<400> SEQUENCE: 8
tgccagaggc tcttgaagtc                                           20
```

METHODS AND COMPOSITIONS FOR THE DIAGNOSIS AND TREATMENT OF CANCER

CROSS-REFERENCE TO RELATED APPLICATIONS

The present application is a divisional application of U.S. Ser. No. 14/869,724 filed Sep. 29, 2015, which claims benefit under 35 USC 119(e) of Chinese Application No. 201410512479.7 filed Sep. 29, 2014, which are incorporated by reference in their entirety for all purposes.

REFERENCE TO A SEQUENCE LISTING

This application includes an electronic sequence listing in a file named 518617_SEQLST.txt, created on Aug. 9, 2018, and containing 1,743 bytes, which is hereby incorporated by reference in its entirety for all purposes.

FIELD OF THE INVENTION

The present invention relates to methods, kits, and compositions for detecting and/or predicting metastatic potential of gastric cancer cells or for evaluating prognosis in a patient with gastric cancer by detection of the protein expression level of an HLA class I molecule and/or the copy number variation of a polynucleotide encoding the HLA class I molecule combined with the number of NK cells at the tumor site. The present invention also relates to the use of the protein expression level of an HLA class I molecule and/or the copy number variation of a polynucleotide encoding the HLA class I molecule as a prognosis biomarker and metastasis predictive biomarker of cancer.

BACKGROUND OF THE INVENTION

Gastric cancer is among the malignancies with highest morbidity worldwide. Most patients with gastric cancer die of metastasis or relapse, leading to high mortality of the disease. Compared with other organs, the stomach tissue contains relatively abundant lymphatic structures, contributing to the relapse and metastasis of gastric cancer via the lymphatic system. The lymphatic system is rich in immune components, proper activation of immune cells can reduce the probability of relapse and metastasis through killing tumor cells. However, tumor cells often escape from the lysis of immune cells, the mechanisms of which are not completely clear. Therefore it is of significant clinical value to design, on the basis of the tumor immune evasion mechanisms, effective immunotherapeutic strategies, which have become another efficient anti-cancer treatment after surgery.

Human immune system can be divided into innate and adaptive components. The adaptive immunity functions through B and T lymphocytes and serves as a secondary response towards specific antigen but usually takes effect after a period of time. Contrary to it, the innate immunity, including natural killer cells (NK cells), is the first line to defense tumor cells and pathogen. NK cells can react and exert cytotoxicity within 4 hours in vitro and in vivo, via release of perforins, NK cytotoxic factors, and tumor necrosis factors. NK cells have been found to lyse tumor cells in a short amount of time, thus recent emphasis has been made on the development and clinical utilization of NK immunity to treat tumor.

The cytotoxic activity mediated by NK cells is intricately regulated by the balance between activating signals and suppressive signals. The proteins of HLA-A, B, and C (i.e., the classic HLA class I molecules) expressed on target cells interact with inhibitory receptors on NK cells and cause anergy. On the other hand, IL-2 and IL-12 secreted by dendritic cells activate NK cells.

Various remedial practices were devised based on the regulation mechanisms in order to achieve tumor regression by altering the suppressed status of NK cells, the most renowned ones including using allogenic NK cells and disrupting the inhibitory receptors on NK surface. These practices significantly enhanced the anti-cancer effects of NK-related immune therapies, but they also gave rise to auto-immune symptoms. Therefore, it remains one of the plausible means of enhancing the outcome of NK therapies to remold the cancer cells.

SUMMARY OF THE INVENTION

In an aspect, the present invention provides a kit for detecting and/or diagnosing metastatic potential of cancer cells or for evaluating prognosis in a patient with cancer comprising a reagent for detecting in a tumor tissue the protein expression level of an HLA class I molecule and/or the copy number variation of a polynucleotide encoding the HLA class I molecule, wherein a higher protein expression level of the HLA class I molecule and/or a copy number amplification of the polynucleotide encoding the HLA class I molecule compared to that in the adjacent matched normal tissue is indicative of high metastatic potential of the cancer cells and/or poor prognosis in the patient; and a lower protein expression level of the HLA class I molecule and/or a copy number deletion of the polynucleotide encoding the HLA class I molecule compared to that in the adjacent matched normal tissue is indicative of low metastatic potential of the cancer cells and/or good prognosis in the patient.

In an embodiment of this aspect of the present invention, the reagent for detecting the protein expression level of the HLA class I molecule and/or the copy number variation of the polynucleotide encoding the HLA class I molecule is a binding agent that binds to the HLA class I molecule or a substance that hybridizes with or amplifies the polynucleotide encoding the HLA class I molecule. In another embodiment of the present invention, binding agent that binds to the HLA class I molecule is an anti-HLA class I antibody, and the HLA class I molecule is HLA-A, HLA-B, or HLA-C. Preferably, the HLA class I molecule is HLA-C. In another embodiment of the present invention, the kit further comprises a reagent for detecting in the tumor tissue the number or cytotoxic activity of NK cells, wherein a higher number or cytotoxic activity of NK cells compared to that in the adjacent matched normal tissue indicates low metastatic potential of the cancer cells and/or good prognosis in the patient. In another embodiment of the present invention, the kit further comprises one or more reagents selected from the group consisting of: (a) a reagent for detecting in the tumor tissue the protein expression level of NKp30, (b) a reagent for detecting in the tumor tissue the protein expression level of pERK, (c) a reagent for detecting in the tumor tissue the protein expression level of IL-2, and (d) a reagent for detecting in the tumor tissue the protein expression level of IL-12, wherein a lower protein expression level of NKp30, pERK, IL-2, IL-12, or any combination thereof compared to that in the adjacent matched normal tissue indicates high metastatic potential of the cancer cells and/or poor prognosis in the patient. In another embodiment of the present invention, the cancer cells are gastric cancer cells, and the cancer is gastric cancer.

A second aspect of the present invention provides a use of a reagent for detecting in a tumor tissue the protein expression level of an HLA class I molecule and/or the copy number variation of a polynucleotide encoding the HLA class I molecule in the manufacture of a kit for detecting and/or diagnosing metastatic potential of cancer cells or for evaluating prognosis in a patient with cancer, wherein a higher protein expression level of the HLA class I molecule and/or a copy number amplification of the polynucleotide encoding the HLA class I molecule compared to that in the adjacent matched normal tissue is indicative of high metastatic potential of the cancer cells and/or poor prognosis in the patient; and a lower protein expression level of the HLA class I molecule and/or a copy number deletion of the polynucleotide encoding the HLA class I molecule compared to that in the adjacent matched normal tissue is indicative of low metastatic potential of the cancer cells and/or good prognosis in the patient.

In an embodiment of this aspect of the present invention, the reagent for detecting the protein expression level of the HLA class I molecule and/or the copy number variation of the polynucleotide encoding the HLA class I molecule is a binding agent that binds to the HLA class I molecule or a substance that hybridizes with or amplifies the polynucleotide encoding the HLA class I molecule. In another embodiment of the present invention, the binding agent that binds to the HLA class I molecule is an anti-HLA class I antibody, and the HLA class I molecule is HLA-A, HLA-B, or HLA-C. In another embodiment of the present invention, the reagent for detecting the protein expression level of the HLA class I molecule and/or the copy number variation of the polynucleotide encoding the HLA class I molecule is combined with a reagent for detecting in the tumor tissue the number or cytotoxic activity of NK cells, wherein a higher number or cytotoxic activity of NK cells compared to that in the adjacent matched normal tissue indicates low metastatic potential of the cancer cells and/or good prognosis in the patient. In another embodiment of the present invention, the reagent for detecting the protein expression level of the HLA class I molecule and/or the copy number variation of the polynucleotide encoding the HLA class I molecule is combined with one or more reagents selected from the group consisting of: (a) a reagent for detecting in the tumor tissue the protein expression level of NKp30, (b) a reagent for detecting in the tumor tissue the protein expression level of pERK, (c) a reagent for detecting in the tumor tissue the protein expression level of IL-2, and (d) a reagent for detecting in the tumor tissue the protein expression level of IL-12, wherein a lower protein expression level of NKp30, pERK, IL-2, IL-12, or any combination thereof compared to that in the adjacent matched normal tissue indicates high metastatic potential of the cancer cells and/or poor prognosis in the patient. In another embodiment of the present invention, the cancer cells are gastric cancer cells, and the cancer is gastric cancer.

A third aspect of the present invention provides a use of an anti-HLA class I antibody or an oligonucleotide that down-regulates the expression of an HLA class I molecule in the manufacture of a medicament for enhancing the effect of NK-cell therapy. In an embodiment of this aspect of the present invention, the medicament further comprises IL-2 and/or IL-12. In another embodiment of the present invention, the medicament further comprises a reagent that activates the NKp30/MAPK3 signaling pathway. In another embodiment of the present invention, the reagent that activates the NKp30/MAPK3 signaling pathway is an oligonucleotide that targets NKp30 ligand BAG6 and up-regulates the expression of BAG6 in cancer cells. In another embodiment of the present invention, the HLA class I molecule is HLA-A, HLA-B, or HLA-C, and the NK-cell therapy is used for treating cancer. In another embodiment of the present invention, the cancer cells express the HLA class I molecule.

A fourth aspect of the present invention provides a composition for detecting and/or diagnosing metastatic potential of cancer cells or for evaluating prognosis in a patient with cancer comprising or consisting of one or more reagents selected from the group consisting of: (a) a reagent for detecting in a sample the protein expression level of an HLA class I molecule and/or the copy number variation of a polynucleotide encoding the HLA class I molecule, (b) a reagent for detecting in the sample the number or cytotoxic activity of NK cells, (c) a reagent for detecting in the sample the protein expression level of IL-2 and/or IL-12, (d) a reagent for detecting in the sample the protein expression level of NKp30, and (e) a reagent for detecting in the sample the protein expression level of pERK. In an embodiment of this aspect of the present invention, the composition comprises: (a) the reagent for detecting in the sample the protein expression level of an HLA class I molecule and/or the copy number variation of a polynucleotide encoding the HLA class I molecule, (b) the reagent for detecting in the sample the number or cytotoxic activity of NK cells. In another embodiment of the present invention, the composition comprises: (a) the reagent for detecting in the sample the protein expression level of an HLA class I molecule and/or the copy number variation of a polynucleotide encoding the HLA class I molecule, and one or more reagents selected from the group consisting of (c) the reagent for detecting in the sample the protein expression level of IL-2 and/or IL-12, (d) the reagent for detecting in the sample the protein expression level of NKp30, and (e) the reagent for detecting in the sample the protein expression level of pERK.

A fifth aspect of the present invention provides a kit for assessing the tumorigenicity of cells or cell lines in an individual comprising: (a) a reagent for detecting in a sample the protein expression level of an HLA class I molecule, and (b) a reagent for detecting in the sample the number or cytotoxic activity of NK cells, wherein a lower protein expression level of the HLA class I molecule and a higher number or cytotoxic activity of NK cells compared to that in a control sample is indicative of no/low tumorigenicity of the cells or cell lines in the individual.

A sixth aspect of the present invention provides a kit for assessing the tumorigenicity of cells or cell lines in an individual comprising: (a) a reagent for detecting in a sample the protein expression level of an HLA class I molecule, and (b) one or more reagents selected from the group consisting of: a reagent for detecting in the sample the protein expression level of NKp30, a reagent for detecting in the sample the protein expression level of pERK, a reagent for detecting in the sample the protein expression level of IL-2, and a reagent for detecting in the sample the protein expression level of IL-12, wherein a higher protein expression level of the HLA class I molecule and a lower protein expression level of NKp30, pERK, IL-2, IL-12, or any combination thereof compared to that in a control sample is indicative of high tumorigenicity of the cells or cell lines in the individual. In an embodiment of this aspect of the present invention, the expression of NKp30 indicates low tumorigenicity of the cells or cell lines. In another embodiment of the present invention, the cells or cell lines are tumor cells of epithelial origin.

In an embodiment of the fifth or sixth aspect of the present invention, the reagent for detecting in a sample the protein expression level of an HLA class I molecule is an anti-HLA class I antibody, and the HLA class I molecule is HLA-A, HLA-B, or HLA-C. In another embodiment of the fifth or sixth aspect of the present invention, the tumor cells are gastric cancer cells. In another embodiment of the fifth or sixth aspect of the present invention, the individual is a human being or a nude mouse.

A seventh aspect of the present invention provides a method for in vitro and/or in vivo detecting and/or diagnosing metastatic potential of cancer cells or for evaluating prognosis in a patient with cancer comprising contacting a cancer cell sample from an individual with a reagent for detecting in the cancer cell sample the protein expression level of an HLA class I molecule and/or the copy number variation of a polynucleotide encoding the HLA class I molecule, wherein a higher protein expression level of the HLA class I molecule and/or a copy number amplification of the polynucleotide encoding the HLA class I molecule compared to that in a control sample is indicative of high metastatic potential of the cancer cells and/or poor prognosis in the patient. In an embodiment of the present invention, the method further comprises contacting the cancer cell sample from the individual with a reagent for detecting in the cancer cell sample the number or cytotoxic activity of NK cells, wherein a higher number or cytotoxic activity of NK cells compared to that in the control sample indicates low metastatic potential of the cancer cells and/or good prognosis in the patient. In another embodiment of the present invention, the method further comprises contacting the cancer cell sample from the individual with one or more reagents selected from the group consisting of: (a) a reagent for detecting in the cancer cell sample the protein expression level of NKp30, (b) a reagent for detecting in the cancer cell sample the protein expression level of pERK, (c) a reagent for detecting in the cancer cell sample the protein expression level of IL-2, and (d) a reagent for detecting in the cancer cell sample the protein expression level of IL-12, wherein a lower protein expression level of NKp30, pERK, IL-2, IL-12, or any combination thereof compared to that in the control sample indicates high metastatic potential of the cancer cells and/or poor prognosis in the patient. In another embodiment of the present invention, the reagent for detecting the protein expression level of the HLA class I molecule and/or the copy number variation of the polynucleotide encoding the HLA class I molecule is a binding agent that binds to the HLA class I molecule or a substance that hybridizes with or amplifies the polynucleotide encoding the HLA class I molecule. In another embodiment of the present invention, the binding agent that binds to the HLA class I molecule is an anti-HLA class I antibody, and the HLA class I molecule is HLA-A, HLA-B, or HLA-C. In another embodiment of the present invention, the cancer cells are gastric cancer cells, and the cancer is gastric cancer.

An eighth aspect of the present invention provides a use of an HLA class I molecule for detecting and/or diagnosing metastatic potential of cancer cells or for evaluating prognosis in a patient with cancer. In an embodiment of this aspect of the present invention, the cancer cells are gastric cancer cells, and the cancer is gastric cancer.

An ninth aspect of the present invention provides a use of one or more reagents selected from a group for detecting and/or diagnosing metastatic potential of cancer cells or for evaluating prognosis in a patient with cancer, wherein the group consists of: (a) a reagent for detecting in a sample the protein expression level of an HLA class I molecule and/or the copy number variation of a polynucleotide encoding the HLA class I molecule, (b) a reagent for detecting in the sample the number or cytotoxic activity of NK cells, (c) a reagent for detecting in the sample the protein expression level of IL-2 and/or IL-12, (d) a reagent for detecting in the sample the protein expression level of NKp30, and (e) a reagent for detecting in the sample the protein expression level of pERK. In an embodiment of this aspect of the present invention, the reagent for detecting in the sample the protein expression level of an HLA class I molecule is an anti-HLA class I antibody, and the HLA class I molecule is HLA-A, HLA-B, or HLA-C. In another embodiment of the present invention, the cancer cells are gastric cancer cells, and the cancer is gastric cancer.

In one of the above aspects of the present invention, the control sample is the adjacent matched normal tissue, which is away from tumor tissue at least 5 cm. In one of the above aspects of the present invention, the control sample is nontumor cells with no or low expression of HLA class I molecule such as cells at peritumoral areas, or tumor cells with no or low expression of HLA class I molecule such as the AGS cell line. In any one of the above aspects of the present invention, the cancer cells or tumor cells are tumor cells of epithelial origin, preferably gastric cancer cells; the cancer is a tumor of epithelial origin, preferably gastric cancer. In another embodiment, the cancer cells or tumor cells express HLA class I molecule.

DESCRIPTION OF THE DRAWINGS

FIG. 2A, CIRCUS diagrams of whole genome sequencing of BGC823 and AGS cells. FIG. 2B, gene copy number of HLA class I molecules in BGC823 and AGS cells. FIG. 2C, Real-time PCR detection of HLA-A, HLA-B, and HLA-C relative copy number in BGC823 and AGS cells.

FIGS. 4A and B, immunoblotting of HLA class I molecules (FIG. 4A) and NKp30/VAV2/MAPK3 signal pathway (FIG. 4B) in BGC823 and AGS cells. FIGS. 4C and D, immunofluorescence of HLA-A, HLA-B and NKp30 in BGC823 and AGS cells (FIG. 4C), and of HLA-C in such cells before and after stimulation of NK cells derived from nude mice (FIG. 4D).

FIGS. 5A-E. NK cells display cytotoxic activity against AGS but not BGC823 cells. FIG. 5A, cytotoxicity of nude mice NK cells against BGC823 and AGS cells in different coculture ratios. FIG. 5B, time-lapse imaging of NK cells lysing of BGC823 and AGS cells. FIG. 5C, Matrigel-coated AGS cells are more resistant to NK attack (left) and more tumorigenic in nude mice (right). FIGS. 5D and E, tumorigenic capacity of BGC823 (FIG. 5D) and AGS (FIG. 5E) cells in NOD/SCID mice that lack NK cells.

FIGS. 6A-E. Critical roles of HLA class I molecules and NKp30/VAV2/MAPK3/IL-12(IL-2) signal pathway in NK-mediated tumor cell lysis. FIGS. 6A and B, cytotoxicity assay (FIG. 6A) and time-lapse imaging (FIG. 6B) of NK-tumor coculture in the presence of IL-12 and antibodies against HLA class I molecules. FIG. 6C, immunoblotting of NKp30/VAV2/MAPK3/IL-12(IL-2) signal pathway in BGC823 and AGS cells. FIG. 6D, immunoblotting of IL-12 in AGS cells under interference of NKp30 expression. FIG. 6E, time-lapse imaging of NK cytotoxicity against AGS cells under interference of NKp30 expression or in the presence of antibodies against IL-12.

FIGS. 7A-C. Expression of classic HLA class I molecules and NKp30/MAPK3/IL-12(IL-2) in various gastric cancer cell lines with different tumorigenic capacity in nude mice. FIGS. 7A and B, real-time PCR detection of copy number variations of HLA class I molecules (FIG. 7A) and immunoblotting of HLA class I molecules and NKp30/MAPK3/IL-12(IL-2) (FIG. 7B) in various gastric cancer cell lines with different tumorigenic capacity in nude mice. FIG. 7C, real-time PCR detection of copy number variations of HLA class I molecules in metastatic and non-metastatic tumor tissues.

FIGS. 8A-F. Expression of HLA class I molecules in paired gastric cancer samples. FIGS. 8A and B, immuno-histochemical detection of HLA class I molecules in tumor tissue and adjacent matched normal tissue (FIG. 8A) and in metastatic and non-metastatic tumor tissues (FIG. 8B) of gastric cancer. FIGS. 8C and D, overall survival in patients with low or high HLA class I expression (FIG. 8C) and in patients with low or high HLA class I combined with high or low NK infiltration (FIG. 8D). FIG. 8E, treatment of tumor in nude mice with anti-HLA class I antibodies reduced the tumor growth rate. FIG. 8F, hematoxylin-eosin staining of tissues of treated and control individuals described in FIG. 8E.

DETAILED DESCRIPTION OF THE INVENTION

Figure 1:
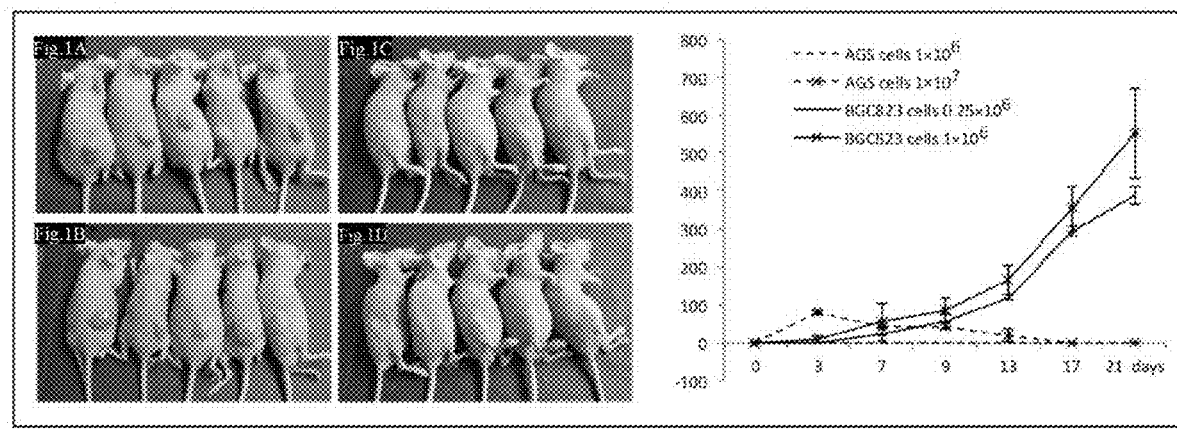
FIG. 1. Tumorigenic capacity of BGC823 and AGS cells in nude mice. Left panel, photographs of nude mice bearing tumors from inoculation of $2.5 \times 10^5$ BGC823 cells (A), $1 \times 10^6$ BGC823 cells (B), $1 \times 10^6$ AGS cells (C), or $1 \times 10^7$ AGS cells (D). Right panel, kinetic growth of the mice-born tumors derived from inoculation of $2.5 \times 10^5$ BGC823 cells, $1 \times 10^6$ BGC823 cells, $1 \times 10^6$ AGS cells, and $1 \times 10^7$ AGS cells.

Several aspects of the invention are described below with reference to examples for illustration. It should be understood that numerous specific details, relationships, and methods are set forth to provide a full understanding of the invention. One skilled in the relevant art, however, will readily recognize that the invention can be practiced without one or more of the specific details, or with other methods, etc.

The present invention relates to the relationship between the expression of a newly found cancer marker (e.g., HLA class I molecules) and metastatic potential of cancer cells or prognosis in patients with cancer. The cancer marker described herein provides means to predict the metastatic potential of cancer cells. Therefore, an embodiment of the present invention represents an improvement of cancer markers, and the cancer marker described herein applies to the diagnosis of common cancers or specific cancers such as gastric cancer. The cancer marker described herein especially applies to the prediction of metastatic potential of gastric cancer cells and prognosis of patients with gastric cancer. In another embodiment, the newly found cancer marker described herein (i.e., HLA class I molecules) can be combined with one or more of the known cancer markers in the field (such as CEA, NSE, CA 19-9, CA 125, CA 72-4, PSA, proGRP, SCC, and NNMT, etc.) or with one or more of the other cancer markers described herein (NK cell, NKp30, pERK, IL-2, IL-12 or their combinations), for treatments, or diagnosis of metastatic potential of cancer cells, or evaluation of prognosis in patients with cancer, or preparation of kits for such uses.

Unless defined otherwise, all technical and scientific terms used herein have the same meanings as commonly understood by one of ordinary skill in the art to which this invention belongs. References to common terminologies in cellular and molecular biology can be found in Lewin, B., Gene VIII, Science Press (2005), ISBN:978-7-03-014597-0; Dudek, R. W., Cell and molecular biology, Chinacitic Press (2004), ISBN:978-7-50-860075-8; Wang, J., Biochemistry, Higher Education Press (2002), ISBN:978-7-04-011088-3; Kendrew, J. et al., The Encyclopedia of Molecular Biology, Blackwell Science Ltd. (1994), ISBN 0-632-02182-9; and Meyers, R. A., Molecular Biology and Biotechnology: a Comprehensive Desk Reference, VCH Publishers, Inc. (1995), ISBN 1-56081-5698. Although any methods and materials similar or equivalent to those described herein can be used in the practice of the invention, particular materials and methods are described herein.

The term "cancer" refers to all types of cancers or neoplasm or malignant tumors found in mammals., examples including but not limited to fibrosarcoma, mucous sarcoma, liposarcoma, chondrosarcoma, osteosarcoma, chordoma, angiosarcoma, endotheliosarcoma, lymphangiosarcoma, lymphangioendothelial sarcoma, synovialoma, mesothelioma, Ewing's tumor, leiomyosarcoma, rhabdomyosarcoma, gastric cancer, colorectal cancer, pancreatic cancer, breast cancer, ovarian cancer, prostatic carcinoma, squamous cell carcinoma, basal cell carcinoma, adenocarcinoma, syringocarcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, testicular cancer, lung cancer, small cell lung cancer, bladder cancer, epicytoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma. In certain aspects of the present invention, the cancer is preferably gastric cancer, more preferably highly tumorigenic or highly metastatic gastric cancer.

The term "cancer cells" or "tumor cells" refers to a certain type of mutated cells that initiate cancer or tumor, and are characterized as unregulated growing, transformed, and metastasizing. In certain aspects of the present invention, the "cancer cells" or "tumor cells" are cancer or tumor cells of epithelial origin, preferably gastric cancer cells, more preferably highly tumorigenic or highly metastatic gastric cancer cells. In several aspects of the present invention, the cancer or tumor cells express HLA class I molecules such as HLA-A, HLA-B, and HLA-C. In certain aspects of the present invention, the gastric cancer cells are highly tumorigenic cells described in the embodiments, such as BGC823, MGC803, SGC7901 and MKN45, etc.

The term "metastatic potential" refers to the ability or possibility of a cancer cell moving from the initial site to other sites in the body.

The term "sample" means a material known or suspected of expressing or containing cancer markers, or binding agents such as antibodies specific for cancer markers (such as HLA class I molecules). The sample may be derived from a biological source ("biological sample"), such as tissues (e.g. biopsy samples), extracts, or cell cultures, including cells (e.g. tumor cells), cell lysates, and biological or physiological fluids, such as, for example, whole blood, plasma, serum, saliva, cerebral spinal fluid, sweat, urine, milk, peritoneal fluid and the like. A sample may be used directly as obtained from the source or following a pretreatment to modify the character of the sample, such as preparing plasma from blood, diluting viscous fluid, and the like. In certain aspects of the invention, the sample is a human physiological fluid, such as human serum. In certain aspects of the invention, the sample is a biopsy sample, such as tumor tissues or cells obtained from biopsy. In certain aspects of the invention, the sample is a malignant or normal tissue sample, such as peritumoral normal tissues or adjacent matched normal tissues.

Samples that may be analyzed in accordance with the invention include polynucleotides from clinically relevant sources. As will be appreciated by those skilled in the art, the target polynucleotides can comprise RNA, including but not limited to total cellular RNA, poly(A)$^+$ messenger RNA (mRNA) or fraction thereof, cytoplasmic mRNA, or RNA transcribed from cDNA (i.e., cRNA).

Target polynucleotides can be detectably labeled at one or more nucleotides using methods known in the art. The detectable label can be, without limitation, a luminescent label, fluorescent label, biological luminescent label, chemical luminescent label, radiolabel, and colorimetric label.

The term "marker" as used herein refers to a molecule to be used as a target for analyzing a patient's test sample. Examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point ($=$PI) or molecular weight ($=$MW), or both e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Non-limiting examples for posttranslational modifications are glycosylation, acylation, and/or phosphorylation.

The expression of the marker can be identified by detection of marker translation (i.e., detection of marker protein in a sample). Methods suitable for the detection of marker protein include any suitable method for detecting and/or measuring proteins from a cell or cell extract. Such methods include, but are not limited to, immunoblot (e.g., Western blot), enzyme-linked immunosorbent assay (ELISA), radioimmunoassay (RIA), immunoprecipitation, immunohistochemistry and immunofluorescence. Particularly preferred methods for detection of proteins include any cell based assay, including immunohistochemistry and immunofluorescence assays. Such methods are well known in the art.

The terms "subject", "patient" and "individual" are interchangeably herein and refer to a warm-blooded animal such as a mammal that is afflicted with, or suspected of having, being pre-disposed to, or being screened for cancer, in particular cancer with metastatic potential. The term includes but is not limited to domestic animals, rodents (such as rats and mice), primates and humans. Preferably, the term refers to a human.

The term "treating", "treatment" or "therapy" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

The terms "polypeptide" and "protein" are used interchangeably herein and indicate at least one molecular chain of amino acids linked through covalent and/or non-covalent bonds. The terms include peptides, oligopeptides, and proteins, and post-translational modifications of the polypeptides, e.g. glycosylations, acetylations, phosphorylations, and the like. Protein fragments, analogues, mutated or variant proteins, fusion proteins, and the like, are also included within the meaning of the terms.

In certain embodiments of the present invention, detection of "protein expression levels", "gene expression", or "gene expression levels" includes but is not limited to detection of corresponding RNA, protein, or polypeptide levels (or their combinations). Specific methods and reagents for the detection of protein, polypeptide, or RNA levels are not restricted in the present invention, and are well known in the field.

Methods for measuring in a sample the quantity or concentration of a protein is known by those skilled in the art. These methods include RIA, competitive binding assay, protein blotting assay, and ELISA. In methods that involve usage of antibodies, both monoclonal and polyclonal antibodies are applicable, and the antibodies are immunologically specific against the protein, the epitope or the fragment.

The term "polynucleotide" refers to a polymeric form of nucleotides of any length, either ribonucleotides or deoxyribonucleotides. The term includes double- and single-stranded DNA and RNA, modifications such as methylation or capping and unmodified forms of the polynucleotide. The terms "polynucleotide" and "oligonucleotide" are used interchangeably herein. A polynucleotide may, but need not, include additional coding or non-coding sequences, or it may, but need not, be linked to other molecules and/or carrier or support materials. Polynucleotides for use in the methods or kit of the invention may be of any length suitable for a particular method or kit. In certain applications the term refers to antisense nucleic acid molecules (e.g. an mRNA or DNA strand in the reverse orientation to a sense of polynucleotides encoding cancer markers of the present invention such as HLA class I molecules).

The polynucleotide cancer markers in the present invention include polynucleotides encoding polypeptide cancer markers (for example, HLA class I molecules), including a native-sequence polypeptide, a polypeptide variant including a portion of the polypeptide cancer marker, an isoform, a precursor, and a chimeric polypeptide. A polynucleotide encoding an HLA class I polypeptide that can be employed in the present invention includes but is not limited to nucleic acids comprising a sequence of GenBank Accession Nos. Z46633, D83043, or D83957 or fragments thereof.

Polynucleotides used in the methods of the invention include complementary nucleic acid sequences and nucleic acids that are substantially identical to these sequences. The polynucleotides also include sequences that differ from a nucleic acid sequence due to degeneracy in the genetic code. Polynucleotides used in the methods of the present invention may also include nucleic acids that hybridize under stringent conditions, preferably high stringency conditions to a nucleic acid sequence of a polynucleotide cancer marker.

Polynucleotide hybridization assays are well known in the art. Hybridization assay procedures and conditions will vary depending on the application and are selected in accordance with the general binding methods known including those referred to in: Sambrook, J., et al., The Condensed Protocols From Molecular Cloning: A Laboratory Manual, Science Press (2002), ISBN:7-03-010338-6; Young and Davis, Proc. Natl. Acad. Sci. USA 80:1194 (1983). Methods and apparatus for carrying out repeated and controlled hybridization reactions have been described in U.S. Pat. Nos. 5,871,928, 5,874,219, 6,045,996, 6,386,749 and 6,391,623 each of are incorporated herein by reference.

Under certain circumstances, the sample may need amplification. A genomic sample may be amplified by a variety of mechanisms, some of which may employ PCR. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, Genomics 4, 560 (1989), Landegren et al. Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al, Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 5,437,975), arbitrarily primed polymerase chain reaction (AP-PCR) (U.S. Pat. Nos. 5,413,909, 5,86,245) and nucleic acid based sequence amplification (NABSA). (See, U.S. Pat. Nos. 5,409,818, 5,554,517 and 6,063,603, each of which is incorporated herein by reference).

A "higher" or "lower" marker expression level or a copy number "amplification" or "deletion" of a polynucleotide encoding the marker in a sample of a patient compared to that in a control or standard (e.g., a normal level, levels in different stages, or levels in other samples of the patient) indicates that the levels in the sample are at least about 1.25, 1.5, 2, 3, 4, 5, 6, 7, 8, 9, or 10 times or more higher, or at most about 1/1.25, 1/1.5, ½, ⅓, ¼, ⅕, ⅙, ⅐, ⅛, ⅑, or ⅒ or less, respectively, than the control or standard. The copy number amplification or deletion may be detected by techniques well known in the field, such as the whole genome sequencing described in the examples.

Reagents for detecting the protein expression level of an HLA class I molecule and/or the copy number variation of a polynucleotide encoding the HLA class I molecule are well known in the field. Such reagents that can be employed in the present invention may be commercially available or prepared through methods well appreciated by those skilled in the art. For instance, in an embodiment of the present invention, such reagent is a binding agent that binds to the HLA class I molecule or a substance that hybridizes with or amplifies the polynucleotide encoding the HLA class I molecule.

The term "binding agent" refers to a substance such as a polypeptide, antibody, ribosome, or aptamer that specifically binds to a cancer marker of the present invention (such as an HLA class I molecule). A substance "specifically binds" to a polypeptide cancer marker in the invention if it reacts at a detectable level with the polypeptide cancer marker, and does not react detectably with peptides containing unrelated sequences or sequences of different polypeptides. Binding properties may be assessed by ELISA, which may be readily performed by those skilled in the art.

A binding agent may be a ribosome, with or without a peptide component, an RNA or DNA molecule, or a polypeptide. A binding agent may be a polypeptide that comprises a polypeptide sequence of a cancer marker HLA class I, a peptide variant thereof, or a non-peptide mimetic of such a sequence.

An aptamer includes a DNA or RNA molecule that binds to nucleic acids and proteins. An aptamer that binds to a cancer marker of the present invention can be produced using conventional techniques, without undue experimentation. For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996).

Antibodies for use in the present invention include but are not limited to synthetic antibodies, monoclonal antibodies, polyclonal antibodies, recombinant antibodies, antibody fragments (such as Fab, Fab', F(ab')$_2$), dAb (domain antibody; see Ward et al., 1989, Nature 341:544-546), antibody heavy chains, intrabodies, humanized antibodies, human antibodies, antibody light chains, single chain Fvs (scFv) (e.g., including monospecific, bispecific, etc.), anti-idiotypic (ant-Id) antibodies, proteins comprising an antibody portion, chimeric antibodies (for example, antibodies which contain the binding specificity of murine antibodies, but in which the remaining portions are of human origin), derivatives, such as enzyme conjugates or labelled derivatives, diabodies, linear antibodies, disulfide-linked Fvs (sdFv), multispecific antibodies (e.g., bispecific antibodies), epitope-binding fragments of any of the above, and any other modified configuration of an immunoglobulin molecule that comprises an antigen recognition site of the required specificity. An antibody includes an antibody of any type (e.g. IgA, IgD, IgE, IgG, IgM and IgY), any class (e.g. IgG1, IgG2, IgG3, IgG4, IgA1 and IgA2), or any subclass (e.g. IgG2a and IgG2b), and the antibody need not be of any particular type, class or subclass. In certain embodiments of the invention the antibodies are IgG antibodies or a class or subclass thereof. An antibody may be from any animal origin including birds and mammals (e.g. human, murine, donkey, sheep, rabbit, goat, guinea pig, camel, horse, or chicken).

By way of example, antibodies used in the invention may be purchased from suppliers such as Santa Cruz Biotechnology (anti-HLA class I antibody, B425 (246-B8.E7), catalog No. sc-59204), ProteinTech Group (anti-HLA-A antibody, catalog Nos. 66013-1-Ig and 15240-1-AP; anti-HLA-B antibody, catalog No. 17260-1-AP; anti-HLA-C antibody, catalog No. 15777-1-AP), Abcam (e.g. antibodies of catalog Nos. ab33252 and ab79523), Epitomics (antibodies of catalog Nos. 1913-1, 2389-1, and 5472-1), and the like. Otherwise, the antibodies may be prepared by recombinant methods well known in the field. In certain embodiments, the antibodies are monoclonal antibodies. See, for example, Kohler et al., Nature 256:495-497 (1975); Kozbor et al., J. Immunol. Methods 81:31-42 (1985); Cote et al., Proc. Natl. Acad. Sci. USA 80:2026-2030 (1983); and Cole et al., Mol. Cell Biol. 62: 109-120 (1984) for the preparation of monoclonal antibodies.

In certain embodiments of the invention, reagents for detecting the protein expression level of an HLA class I molecule and/or the copy number variation of a polynucleotide encoding the HLA class I molecule may be obtained through methods and systems described in CN1703624A. In some other embodiments, the reagents are peptides/antibodies or polynucleotides identified in CN101287755A, WO2012176879, or WO 2011037160, or prepared by methods described in CN101287755A, WO2012176879, or WO 2011037160.

Reagents that may be used for detecting the number or cytotoxic activity of NK cells are well known in the field. Such reagents applicable in the present invention may be purchased or routinely prepared through methods well known by those skilled in the art. By way of example, such reagents may be those used in NK cell number detection by flow cytometry, those used in NK cytotoxic activity examination by MTT colorimetric assay (see, for example, Mosmann T., 1983, J. Immunol. Methods 65:55), LDH determination method (see, for example US4006061 A), and $^{51}$Cr release assay (see, for example, Mariana M. Mata., 2014, J. Immunol. Methods 406:1-9).

Likewise, reagents for detecting NKp30, pERK, IL-2 and IL-12 are well known in the field. Such reagents applicable in the present invention may be purchased or routinely prepared through methods well known by those skilled in the art.

While various embodiments of the present invention have been described above, it should be understood that they have been presented by way of example only, and not of limitation. Those of skill in the art should, in light of the present disclosure, appreciate that many changes can be made in the specific embodiments which are disclosed and still obtain a like or similar result without departing from the spirit and scope of the invention. All references, including publications, patent applications, and patents, cited herein are incorporated by reference in their entirety and to the same extent as if each reference were individually and specifically indicated to be incorporated by reference and were set forth in its entirety herein.

EXAMPLES

Unless specified otherwise, all materials used in the examples were commercially available and were of analytical grade at least, and all specific experimental procedures employed were conventional methods in the field (see, for example, Ausubel, F. M., et al., Short Protocols in Molecular Biology, Science Press (1999), ISBN:7-03-006408-9; and Sambrook, J., et al., The Condensed Protocols From Molecular Cloning: A Laboratory Manual, Science Press (2002), ISBN:7-03-010338-6), and may be determined routinely under necessity by those skilled in the art. Details in certain materials and methods are described below.

Materials and Methods

1. Antibodies

Anti-HLA-A antibody (1913-1; Epitomics), anti-HLA-B antibody (2389-1; Epitomics), anti-HLA-C antibody (5472-1; Epitomics), anti-MICA antibody (T3305; Epitomics), anti-VAV2 antibody (B1241; anbo), anti-MAPK3 antibody (C11133; anbo), anti-NKp30 antibody (BS3888; Bioworld), anti-pERK antibody (Tyr204) (sc-7383; Santa Cruz), anti-BAG6 antibody (6763; Epitomics), anti-actin antibody (A5441; Sigma).

2. Cell Lines

All cell lines were purchased from ATCC or the cell bank of Xiehe Hospital, Beijing.

3. Quantitative Real-time PCR (qPCR)

Primers:

| Gene | Forward (5'-3') | Reverse (5'-3') |
| --- | --- | --- |
| LINE-1 | AAAGCCGCTCAACTACATGG | TGCTTTGAATGCGTCCCAGAG |
| HLA-A | GTAAGGAGGGAGATGGGGGT | CAGCAATGATGCCCACGATG |
| HLA-B | TGAGATGGGGTAAGGAGGGG | CACAACTGCTAGGACAGCCA |
| HLA-C | GTCCAGAACCCACAACTGCT | TGCCAGAGGCTCTTGAAGTC |

The qPCR experiments were performed using cDNA of gastric cancer cell lines or paired gastric cancer samples. Data obtained were analyzed by $2^{-\Delta\Delta Ct}$ interpretation through ABI SDS Software, using LINE-1 as reference.

4. Whole Genome Sequencing (WGS)

WGS of paired-end whole-genome shotgun reads were obtained. Reads were aligned to the reference genome (National Center for Biotechnology Information Build 37) with Burrows-Wheeler Aligner. The copy number variations (CNVs) were predicted by ReadDepth (C. A. Miller, O. Hampton, C. Coarfa, A. Milosavljevic, 2011, ReadDepth: a parallel R package for detecting copy number alterations from short sequencing reads. PloS one 6, e16327). Two copies of chromosome 4 were suggested in the two cell lines when the assessment was accomplished by karyotype and sequencing depth analysis. Obtained fragment ratios were normalized by the copy number of chromosome 4. The CNV was identified as amplification at $\log_2$ ratio>0.45 and deletion at $\log_2$ ratio<0.45, respectively.

5. Immunohistochemistry

Paraffin sections were deparaffinized in xylene twice, 30 min each, and then were transferred to 100%, 95%, 90%, 85%, and 80% alcohol respectively for 5 min each for rehydration. After rinsed in ddH$_2$O thrice, the slides were submerged in 10 mM citrate buffer (pH 6.0) and antigen retrieval was performed with microwave heating. After rinsed in ddH$_2$O thrice, the sections were incubated in 3% H$_2$O$_2$ solution at room temperature for 10 min to block endogenous peroxidase activity. After rinsed in PBS twice, sections were blocked with 5% milk for 30 min at room temperature. Appropriately diluted primary antibodies were added to the PBS-rinsed sections and the slides were incubated in a humidified chamber at 4° C. overnight and were washed in PBS thrice. Appropriately diluted biotinylated secondary antibodies were added to the sections and the slides were incubated in a humidified chamber at room temperature for 30 min and were washed in PBS thrice. Appropriately diluted Streptavidin-HRP conjugates were added to the sections and the slides were incubated in a humidified chamber at room temperature for 30 min in the dark. DAB substrate solution was applied after the sections were washed in PBS thrice and the color of antibody staining was revealed. The reaction was terminated in PBS and sections were washed in tap water. Slides were counterstained by Hematoxylin and decolorized in hydrochloric acid-alcohol, and then blued in weak alkaline water. The slides were then dehydrated through 80%, 85%, 90%, 95%, and 100% alcohol, cleared in xylene for 5 min, and mounted with resinene. Staining was observed under microscopy.

6. Statistical Analyses

Data were subjected to statistical analysis using SPSS 16.0 software (Chicago). Gene expression was compared in different samples using Chi-square ($X^2$) test and t-test. Prognostic analyses were performed with Kaplan-Meier methods and Cox multivariate model. P<0.05 was considered statistically significant.

7. Animal Model

Several human tumor cell lines are tumorigenic in nude mice that lack thymus and T cell immunity. Still, some xenografts are not able to form tumor mass in nude mice, which we speculate is due to host NK activity. Clinical studies have shown that a proportion of cancer patients are not responsive to NK transfusion therapies, the mechanism of which remains unclear. To address this problem, here in the invention we used nude mice as animal models, the highly tumorigenic gastric cell line BGC823 and the non-tumorigenic AGS as tumor cell models, and investigated the mechanisms by which tumor cells evade NK cytotoxicity. The goal was achieved by comparing the genome sequencing data of the two cell lines thereby identifying the key genetic factors that caused AGS cells being targeted for and BGC823 escaping NK-mediated cytolysis. We examined the clinical significance of these key factors in mass samples and preliminarily explored their clinical application.

Example 1

Tumor Formation in Nude Mice

In order to examine the relationship between tumor cell line tumorigenicity in nude mice and NK cell activity, and to study the mechanism by which tumor cells evade NK cytotoxicity, selection of tumor cell lines with high tumorigenicity and non-tumorigenicity in nude mice was a necessary approach. We evaluated the tumorigenicity of tumor cell lines by subcutaneous injection of different numbers of cells of the cell lines. As shown in FIG. 1 and Table 1, cell line BGC823 proved to be highly tumorigenic in that 100% tumor incidence was observed on Day 11 when the injected cell number was $2.5 \times 10^5$; AGS cells, on the other hand, failed to form a tumor mass in 120 days after injection with injected cell numbers up to $1 \times 10^7$. Accordingly, we chose the highly tumorigenic BGC823 cell line and the non-tumorigenic AGS cell line as objects of study.

TABLE 1

Tumor formation of BGC823 and AGS cells in nude mice

| injected Cell line | Cell number | | | | | |
|---|---|---|---|---|---|---|
| | $0.25 \times 10^6$ | $0.3 \times 10^6$ | $0.5 \times 10^6$ | $1 \times 10^6$ | $5 \times 10^6$ | $1 \times 10^7$ |
| BGC823 | 4/4 (11 d) | 63/66 (10 d) | 18/19 (7 d) | 4/4 (3 d) | — | — |
| AGS | — | — | — | 0/3 (90 d) | 0/11 (20 d) | 0/10 (120 d) |

Example 2

Figure 2A:
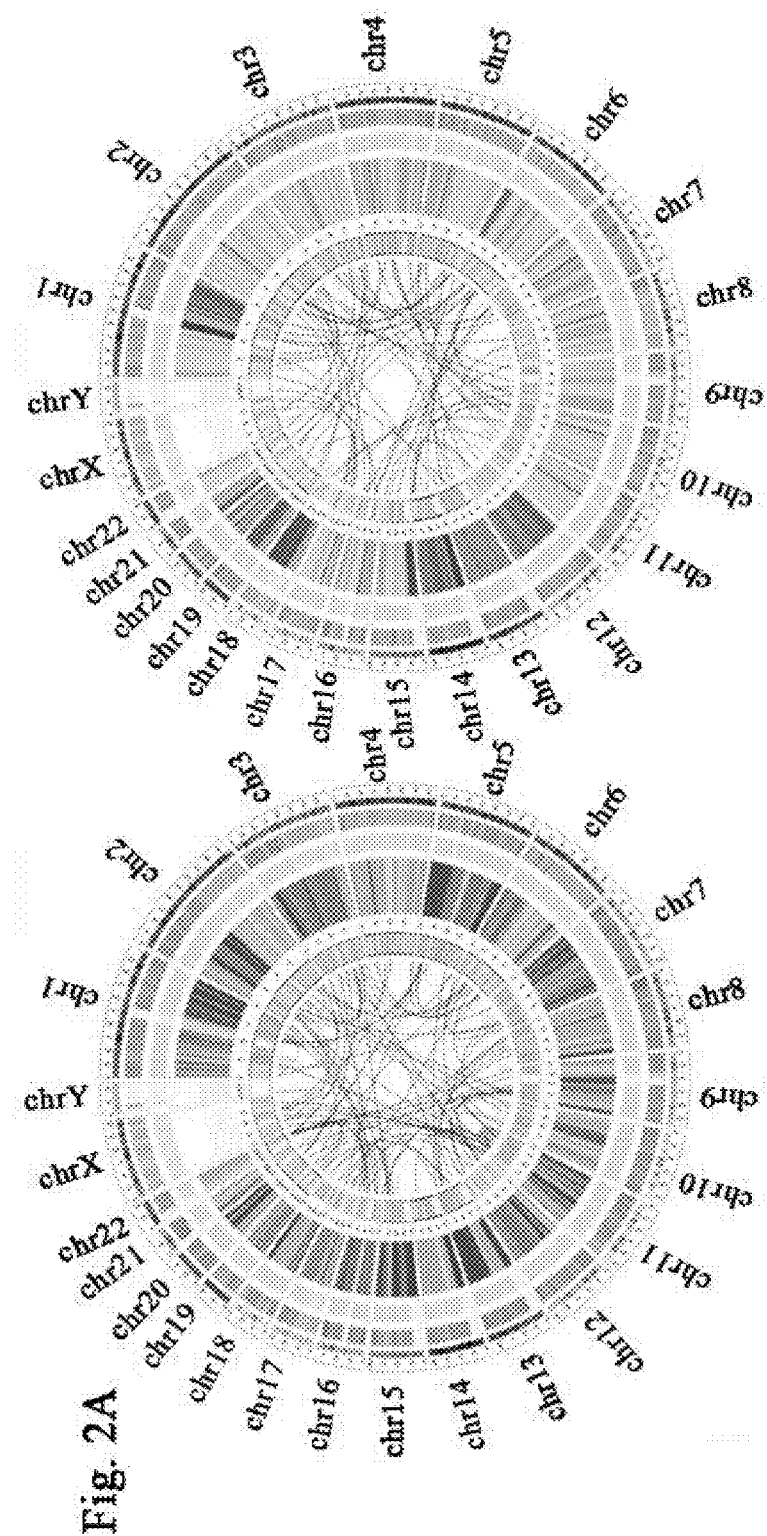
FIGS. 2A-C. Copy number variations (CNVs) in genes in BGC823 and AGS cells.
Figure 2B:
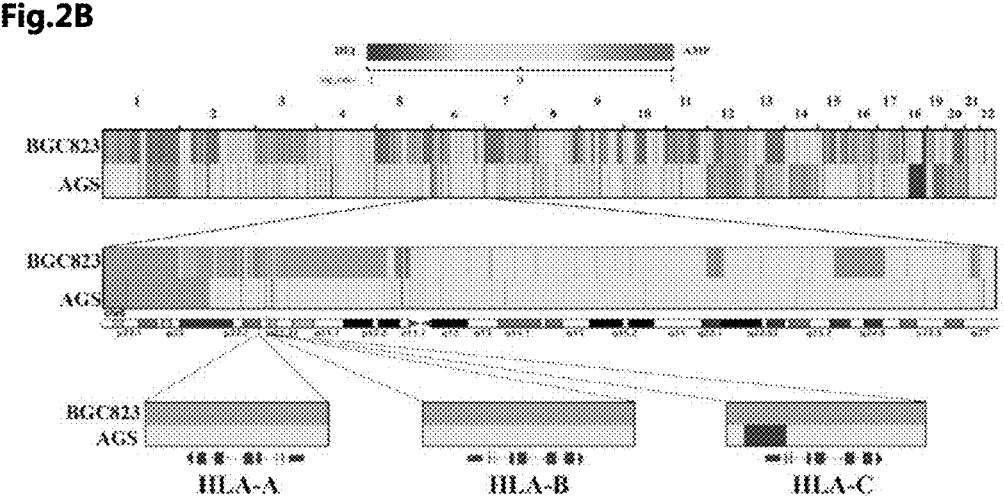
Figure 2C:
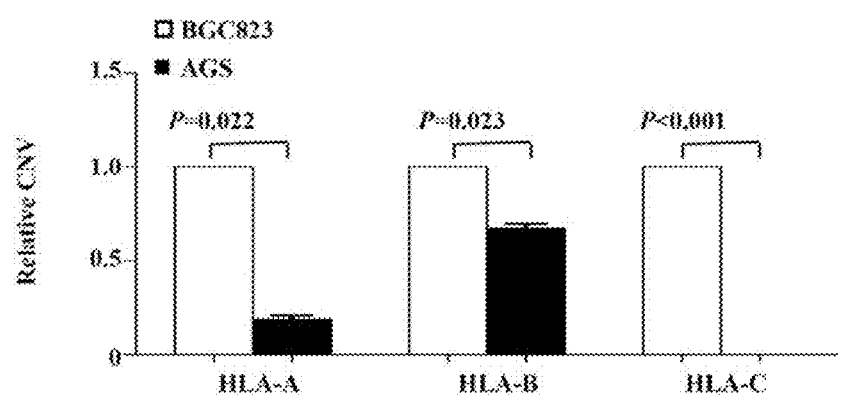

Analysis of CNV Between BGC823 and AGS and Identification of NK Cytotoxicity-Related Genes Previous studies have shown that gene mutations and chromosome anomalies are key events in tumor pathogenesis. Many studies showed that variations in gene copy number were more constant than gene mutations in the onset and development of cancer. Thus we examined the copy number variations between the two cell lines by whole genome sequencing. FIG. 2A showed great disparity between copy numbers of the two cell lines: BGC823 was triploid while AGS was diploid. NK cells are known to target cells with no or low expressions of HLA class I molecules (mainly HLA-A, HLA-B and HLA-C), hence we specifically analyzed the HLA class I region on Chromosome 6 of the two cell lines. As shown in FIG. 2B, there was evident amplification of the region in the BGC823 genome, while deletion of HLA-C was observed in AGS. This result was confirmed by real-time PCR (FIG. 2C) which revealed significantly higher expression of HLA class I molecules in BGC823 cells than in AGS cells.

Figure 3:
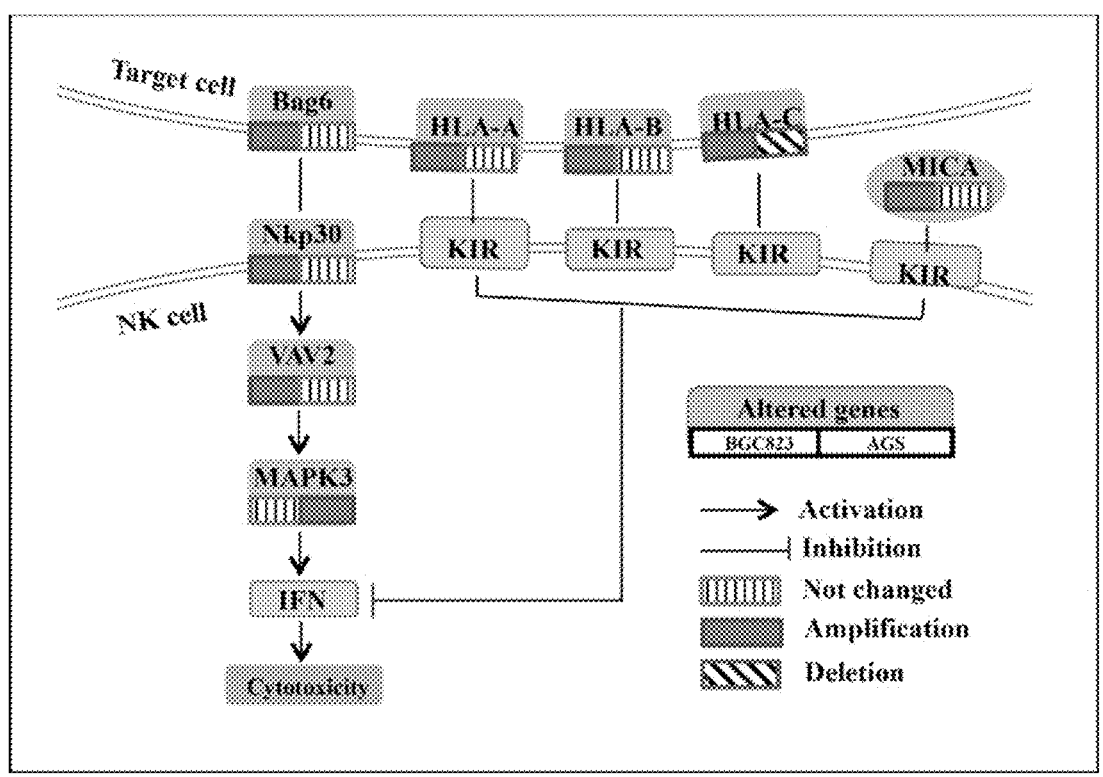
FIG. 3. Diagram of signal pathways involved in NK cytotoxicity and copy number variations of NK cytotoxicity-related genes in BGC823 and AGS cells.

To identify more NK cytotoxicity-related genes, we conducted a KEGG analysis on genes with CNV and found a series of related genes (FIG. 3): HLA class I molecules are expressed on the surface of target cells and interact with inhibitory receptors (killer-cell immunoglobulin-like receptors, KIRs) on NK cells, thereby suppress NK cytotoxicity against the target tumor cells. Ligand BAG6 is expressed by target cells, BAG6 can activate NKp30 on NK cells and the downstream VAV2/MAPK3 pathway, which leads to interferon production by NK cells and subsequent cytotoxicity against target cells.

Example 3

Examination of Protein Expression of the NK Cytotoxicity-Related Genes with CNV

Figure 4A:
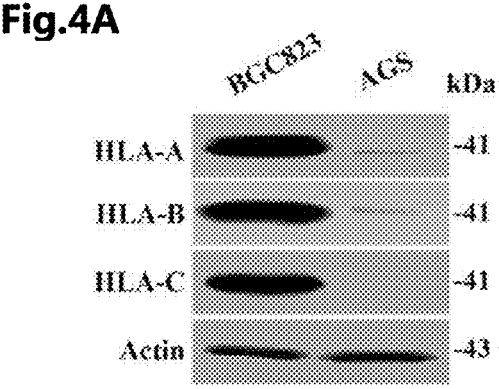
FIGS. 4A-D. Expression of proteins involved in NK cytotoxicity and their subcellular localizations in BGC823 and AGS cells.

As proteins are the ultimate executors of gene functions, we examined the levels of the protein products of the above mentioned cytotoxicity-related genes that with CNV, and established their subcellular localizations by immunofluorescence. As shown in FIG. 4A, the protein expressions of HLA class I molecules were evidently higher in BGC823 than in AGS cells, which is consistent with the copy number data. The fluorescence signals revealed membrane distribution patterns of HLA-A and HLA-B in BGC823 cells but only weak expression of these proteins in AGS cells (FIG. 4C). Upon stimulation from nude mice NK cells, HLA-C molecules in BGC823 cells translocated from cytoplasm to cell membrane, while in AGS cells, no such molecule was detected before and after NK stimulation, and AGS cells displayed apoptotic morphology after NK contact, suggesting active NK cytotoxicity against these AGS cells (FIG. 4D).

Figure 4B:
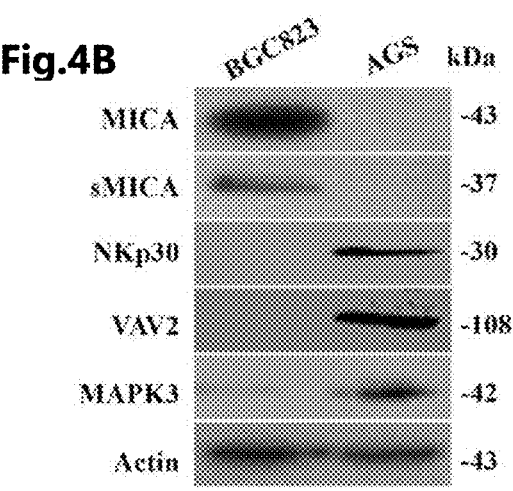
Figure 4C:
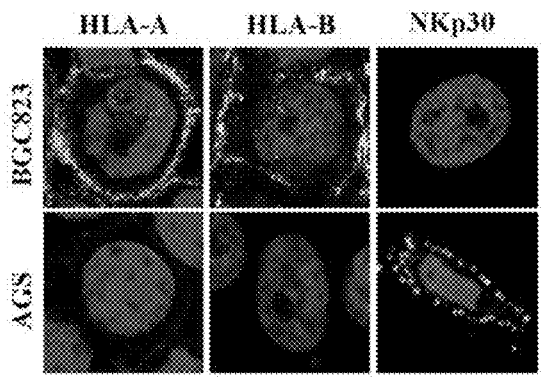
Figure 4D:
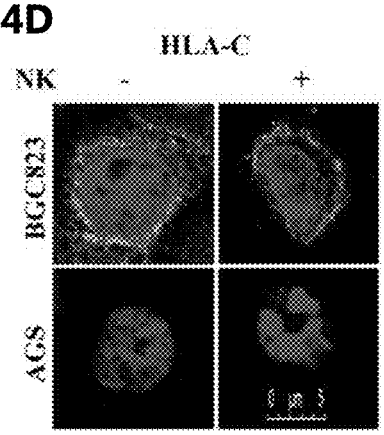

In accordance with the KEGG analysis, we subsequently detected the protein expression of other NK cytotoxicity-related genes (FIG. 4B). NKp30 was reported to be expressed only on NK cells in previous studies. Our results, however, showed evident expression of this molecule on the cell membrane of AGS cells which are non-tumorigenic in nude mice (FIGS. 4B-C). Also in AGS cells, higher levels of NKp30 downstream VAV2 and MAPK3 was detected, compared with those in BGC823 cells, suggesting existence of NK activation pathways inside non-tumorigenic tumor cells, which might be the cause of these cells being susceptible to NK attacks.

Example 4

Examination of Nude Mice NK Cytotoxicity Against Highly Tumorigenic BGC823 Cells and Non-Tumorigenic AGS Cells The results above have established the following phenomena: expression of HLA class I genes that inhibit NK activity is elevated in highly tumorigenic BGC823 cells but down-regulated in non-tumorigenic AGS cells; NK activation pathways are inactive in highly tumorigenic BGC823 cells but active in non-tumorigenic AGS cells; following nude mice NK cell stimulation, apoptotic bodies can be observed in AGS cells. These evidences suggest that NK cytotoxicity against AGS cells might be the cause of the non-tumorigenicity of AGS cells in nude mice. To demonstrate this hypothesis, we isolated NK cells from nude mice and cocultured them with BGC823 and AGS cells. Cytotoxicity assays showed that NK cells lysed AGS cells and that this was NK-cell number dependent; however, NK cells did not react to BGC823 cells (FIG. 5A). Using time-lapse imaging, we observed that NK cells recognized and attacked AGS cells as soon as they were mixed together, but they had no detectable response towards BGC823 cells (FIG. 5B). We subsequently coated AGS cells with Matrigel to separate them from NK cells and then conducted cytotoxicity assays and tumor formation in nude mice. Under these conditions, the extent of lysis for AGS cells was lower compared with uncoated AGS cells; AGS cells coated with Matrigel even acquired tumorigenic capacity in nude mice (FIG. 5C). To further confirm the hypothesis, NOD/SCID mice, which lacked NK immunity, were injected with BGC823 or AGS cells. As shown in 100% tumor incidence was observed for both cell lines in NOD/SCID mice. These results reveal that cytotoxicity of NK cells resulted in AGS cells failing to form tumors in nude mice.

Example 5

High Expression of HLA Class I in Tumor Cells Fosters Evasion of NK Cytotoxicity To clarify the mechanism of NK cells lysing AGS cells but not BGC823 cells, the role of HLA class I molecules was studied first. NK cytotoxicity assays were conducted under blocking of HLA-A, HLA-B and HLA-C by specific antibodies, and as shown in FIG. 6A, NK cells were able to lyse BGC823 cells in the presence of anti-HLA class I antibodies and recombinant NK-activating cytokine IL-12. For AGS cells, there was little difference between the control and treatment groups because of the low expression of HLA class I. NK's cytolytic effects on BGC823 cells following incubation with IL-12 and antibodies against HLA class I was further confirmed by time-lapse imaging (FIG. 6B).

Example 6

Activation of NKp30/VAV2/MAPK3/IL-12 Pathway Promotes NK Cytotoxicity Against Tumor Cells There are many types of somatic cells, such as erythrocytes, expressed low levels of HLA molecules on the surface but will not be targeted by NK cells, which suggests activating mechanisms apart from HLA inhibitory signals in the regulation of NK activity. In immune cells, activation of NKp30/VAV2/MAPK3/IL-12(IL-2) pathway may lead to IL-12/IL-2 production, which may activate NK cells. Previous studies reported expression of NKp30 only on the surface of immune cells, but we found NKp30 expressed on the cell membrane of the non-tumorigenic AGS cells, though not on BGC823 cells which are highly tumorigenic (FIG. 4C). We also found that NKp30 ligand BAG6 was expressed in AGS cells but not in BGC823 cells (FIG. 6C). Levels of downstream molecules of NKp30 signals pERK and IL-12 were also significantly higher in AGS cells than in BGC823 cells (FIG. 6C). Moreover, IL-12 in AGS was down-regulated when NKp30 expression was interfered (FIG. 6D). Time-lapse imaging showed that NK cells did not lyse AGS cells when expression of NKp30 was knocked down, or when IL-12 was blocked with a specific antibody (FIG. 6E). These data indicate that AGS cells up-regulate IL-12 production by activation of NKp30/MAPK3 pathway, which in turn promotes NK cytotoxicity against AGS cells; this pathway is necessary in NK-mediated tumor cell lysing.

Example 7

Expression of Classic HLA Class I Family and NKp30/MAPK3/IL-12(IL-2) in Other Gastric Cancer Cells with Different Tumorigenic Capacity To examine whether the expression pattern of classic HLA class I and NKp30 also existed in other gastric cancer cell lines with different tumorigenic capacity, five other gastric cancer cell lines were investigated. The cell lines MGC803, SGC7901, and MKN45 exhibited high tumorigenicity similar to BGC823 cells, while N87 and KATOIII cells, similar to AGS cells, exhibited low tumorigenicity in nude mice. Real-time PCR was employed to determine CNV of HLA-A, HLA-B and HLA-C in these cell lines, and as shown in FIG. 7A, higher copy numbers of HLA class I were seen in cell lines with high tumorigenicity. Immunoblotting was then used to detect the protein levels of HLA class I and NKp30/MAPK3/IL-12(IL-2) pathway, which confirmed the finding in the qPCR experiment (FIG. 7B). In contrast, protein levels of BAG6, NKp30, pERK, IL-12, and IL-2 were higher in cells with low tumorigenicity (FIG. 7B). These results suggest that the copy numbers of HLA class I molecules, or the protein expression levels of HLA class I molecules and NKp30/MAPK3/IL-12(IL-2) pathway may be used for predicting the tumorigenic capacity of cancer cell lines in nude mice.

Example 8

CNVs and Expression Levels of Classic HLA Class I Molecules in Paired Gastric Cancer Tissues To assess the clinical significance of HLA class I, we conducted immunohistochemical analysis of tumor tissues and the adjacent matched normal tissues from 100 cases of gastric cancer. We found that the expression of HLA-A, HLA-B and HLA-C was significantly higher in the tumor tissue than in the adjacent matched normal tissue area (FIG. 8A; Table 2), which suggests an association between HLA class I expression and tumorigenesis. Further analysis revealed that lowly expressed classic HLA class I was associated with non-metastasis (both lymph node and distant; P=0.005; Table 3; FIG. 8B), as studies in cell lines have shown high consistency between the copy number and the protein expression of HLA class I. Thus we divided the patient samples into metastatic and non-metastatic groups and examined the CNV of HLA class I. As shown in FIG. 7C, HLA class I copy numbers in non-metastatic tumor tissues were lower than in nontumor tissues of the group, while in the metastatic group tumor tissues contained higher copy numbers of HLA class I, suggesting that HLA class I copy number may be used for predicting the metastatic potential of gastric cancer. Survival analysis showed that highly expressed classic HLA class I was an independent predictor for poor prognosis (P=0.008, HR=2.758, 95% CI=1.3-5.8; FIG. 8C). We also examined the NK infiltration in these samples, and found that a combination of NK infiltration with lowly expressed classic HLA class I exhibited a higher degree of association with non-metastasis than lowly expressed classic HLA class I alone (P<0.001 vs P=0.005; Table 3). Furthermore, we found that combining NK cells infiltration with classic HLA class I expression performed even better in predicting patient prognosis (FIG. 8D).

TABLE 2

Immunohistochemical analysis of HLA class I expression in gastric cancer tissues

| Histology | HLA class I expression | | Total case number | P value |
|---|---|---|---|---|
| | Negative | Positive | | |
| Nontumor | 62 (62.0%) | 38 (38.0%) | 100 | 0.001 |
| Tumor | 38 (38.0%) | 62 (62.0%) | 100 | |

TABLE 3

Association between metastasis and histological features in gastric cancer patients

| Feature | | Metastasis | | Total case number | P value |
|---|---|---|---|---|---|
| | | − | + | | |
| HLA class I expression | Positive | 9 (14.5%) | 53 (85.5%) | 62 | 0.005 |
| | Negative | 15 (39.5%) | 23 (60.5%) | 38 | |
| Low HLA Plus NK infiltration | Yes | 14 (50.0%) | 14 (50.0%) | 28 | <0.001 |
| | No | 10 (13.9%) | 62 (86.1%) | 72 | |

Example 9

Antagonizing HLA Class I May Enhance the Effect of NK Immunotherapy

Above data suggested that targeting classic HLA class I expression might enhance the effect of NK therapy. To test this hypothesis, we treated tumor-bearing mice with IL-12 and treated tumor with antibody against HLA class I (treatment group) or IgG (mock group). Compared with control, a drastic inhibition of tumor growth was observed in treatment group (FIG. 8E). Hematoxylin and eosin (HE) staining of tissue in responsive individuals showed that immune cell infiltrated and surrounded tumor cells (FIG. 8F). This result indicates that combined treatment of IL-12 and antibody against HLA class I enhance NK immunotherapy.

What is claimed is:

1. A method for detecting and/or diagnosing metastatic potential of gastric cancer cells or for evaluating prognosis in a patient with gastric cancer comprising
  (i) detecting in a gastric tumor tissue from the patient a copy number variation of a polynucleotide encoding the HLA class I molecule,
    wherein a copy number amplification of the polynucleotide encoding the HLA class I molecule compared to that in the adjacent matched normal tissue is indicative of high metastatic potential of the cancer cells and/or poor prognosis in the patient; and
    a copy number deletion of the polynucleotide encoding the HLA class I molecule compared to that in the adjacent matched normal tissue is indicative of low metastatic potential of the cancer cells and/or good prognosis in the patient;
  wherein the HLA class I molecule is HLA-A, HLA-B, or HLA-C;
  (ii) detecting in the tumor tissue the number or cytotoxic activity of NK cells, wherein a higher number or cytotoxic activity of NK cells compared to that in adjacent matched normal tissue indicates low metastatic potential of the cancer cells and/or good prognosis in the patient; and
  (iii) performing one or more of the following steps:
    (a) detecting in the tumor tissue the protein expression level of NKp30, (b) detecting in the tumor tissue the protein expression level of pERK,
(c) detecting in the tumor tissue the protein expression level of IL-2, and
(d) detecting in the tumor tissue the protein expression level of IL-12,
wherein a lower protein expression level of NKp30, pERK, IL-2, IL-12, or any combination thereof compared to that in the adjacent matched normal tissue indicates high metastatic potential of the cancer cells and/or poor prognosis in the patient.

2. The method of claim 1, wherein the copy number variation of the polynucleotide encoding the HLA class I molecule is detected with a substance that hybridizes with or amplifies the polynucleotide encoding the HLA class I molecule.

* * * * *

UNITED STATES PATENT AND TRADEMARK OFFICE
CERTIFICATE OF CORRECTION

PATENT NO. : 10,962,545 B2  
APPLICATION NO. : 16/102587  
DATED : March 30, 2021  
INVENTOR(S) : Rui Xing et al.

Page 1 of 1

It is certified that error appears in the above-identified patent and that said Letters Patent is hereby corrected as shown below:

On the Title Page

Insert the following after item (62):  
--(30) Foreign Application Priority Data  
Sept. 29, 2014 (CN) ................2014 1 0512479.7--

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*